(12) United States Patent  
Larsson et al.

(10) Patent No.: US 7,709,526 B2
(45) Date of Patent: May 4, 2010

(54) USE OF CYCLOLIGNANS AND NEW CYCLOLIGNANS

(75) Inventors: Olle Larsson, Taby (SE); Magnus Axelson, Hasselby (SE)

(73) Assignee: Biovitrum AB, Stockholm (SE)

( * ) Notice: Subject to any disclaimer, the term of this patent is extended or adjusted under 35 U.S.C. 154(b) by 602 days.

(21) Appl. No.: 11/346,294

(22) Filed: Feb. 3, 2006

(65) Prior Publication Data

US 2006/0154982 A1 Jul. 13, 2006

Related U.S. Application Data

(62) Division of application No. 10/480,800, filed as application No. PCT/SE02/01223 on Jun. 19, 2002, now abandoned.

(60) Provisional application No. 60/300,431, filed on Jun. 26, 2001.

(30) Foreign Application Priority Data

Jun. 19, 2001 (SE) .................................... 0102168

(51) Int. Cl.
*A61K 31/335* (2006.01)
*C07D 317/70* (2006.01)
(52) U.S. Cl. ...................... 514/463; 549/432
(58) Field of Classification Search ................. 549/432; 514/463
See application file for complete search history.

(56) References Cited

U.S. PATENT DOCUMENTS

| 2,825,730 | A | 3/1958 | Prill |
| 4,342,777 | A | 8/1982 | Jurd |
| 2004/0167208 | A1 | 8/2004 | Larsson et al. |
| 2004/0186169 | A1 | 9/2004 | Larsson et al. |

FOREIGN PATENT DOCUMENTS

| CN | 1075316 A | 8/1993 |
| EP | 0 188 248 | 7/1986 |
| JP | 61-267541 | 11/1986 |
| JP | 62-501360 | 4/1987 |
| JP | 09-194368 | 7/1997 |
| JP | 09194368 | 7/1997 |
| SE | 468 213 | 11/1992 |
| WO | 86/04062 | 7/1986 |
| WO | 99/28347 | 6/1999 |
| WO | WO 00/00238 | 1/2000 |
| WO | 01/52826 | 7/2001 |
| WO | 02/40489 | 5/2002 |

OTHER PUBLICATIONS

U.S. Appl. No. 11/346,294, filed Feb. 3, 2006, Larsson, et al.

(Continued)

*Primary Examiner*—Janet L. Andres
*Assistant Examiner*—Raymond Covington
(74) *Attorney, Agent, or Firm*—Oblon, Spivak, McClelland, Maier & Neustadt, P.C.

(57) ABSTRACT

Compounds which inhibit the insulin-like growth factor-1 receptor (IGF-1 R) and methods for using them for treating IGF-1 R dependent diseases, such as cancer.

10 Claims, 3 Drawing Sheets

Deoxypodophyllotoxin

Acetylpodophyllotoxin

Podophyllotoxin

Epipodophyllotoxin

OTHER PUBLICATIONS

U.S. Appl. No. 10/554,399, filed Oct. 24, 2005, Axelson, et al.
U.S. Appl. No. 60/300,461, filed Feb. 26, 2001, Larsson, et al.
U.S. Appl. No. 60/468,054, filed May 6, 2003, Axelson, et al.
Planta Medica, vol. 59, No. 3, p. 246-249.
Foreign Medicine, Physiology, Pathology Science and Clinical Fascicule 19(6), pp. 441-443.
Journal of China University of Science and Technology, vol. 27, No. 1, pp. 113-116 (with English Abstract, Li Qianron, et al.).
Chemical Journal of Chinese Universities, vol. 18, No. 7, pp. 1061-1066 (with English Abstract, Wang Yan-Guang, et al.).
A. San Feliciano, et al., "Antineoplastic and Antiviral Activities of Some Cyclolignans", Planta Medica, vol. 59, No. 3, pp. 246-249, 1993.
Ole Buchardt, et al., "Thermal Chemistry of Podophyllotoxin in Ethanol and a Comparison of the Cytostatic Activity of the Thermolysis Products", Journal of Pharmaceutical Sciences, vol. 75, No. 11. pp. 1076-1080 1986.
Marina Gordaliza, et al., "Antineoplastic and Antiviral Activities of Podophyllotoxin Related Lignans", Arch. Pharm. vol. 327, No. 3, pp. 175-179 1994.
Miriam Novelo, et al., "Cytotoxic constituents from hyptis verticillata", Journal of Natural Products, vol. 56, No. 10, pp. 1728-1736 1993.
J. M. Miguel del Corral, et al., "Methyl ethers of podophyllotoxin-related cyclolignans", Journal of Natural Products, vol. 58, No. 6, pp. 870-877 1995.
Marina Gordaliza, et al., "Synthesis and antineoplastic activity of cyclolignan aldehydes", Eur. J. Med. Chem. vol. 35, No. 7 & 8, pp. 691-698 2000.
Marina Gordaliza, et al.,"Immunosuppressive Cyclolignans", J. Med. Chem. vol. 39, No. 14, pp. 2865-2868 1996.
Marina Gordaliza, et al., "Preparation and Cytotoxicity of Podophyllotoxin Derivatives Lacking the Lactone Ring", Tetrahedron, vol. 53, No. 46, pp. 15743-17560 1997.
Marina Gordaliza, et al., "Selective cytotoxic cyclolignans", Bioorganic & Medicinal Chemistry Letters, vol. 5, No. 21, pp. 2465-2468 1995.
STN International, File CAPLUS, CAPLUS accession No. 1985:125095, Document No. 102:125095, Batra, Janendra K. et al: "Structure-function studies with derivatives of 6-benzyl-1,3-benzodioxole, a new class of synthetic compounds which inhibit tubulin polymerization and mitosis"; & Mol. Pharmacol. (1985), 27(1), 94-102.
STN International, File CAPLUS, CAPLUS accession No. 1987:575915, Document No. 107:175915, Jurd, Leonard et al:"In vivo antitumor activity of 6-benzyl-1,3-benzodioxole derivatives against the P388, L1210, B16, and M5076 murine models"; J. Med. Chem. (1987), 30(10), 1752-6.
S. Shashlkanth, et al., "Synthesis of podophyllotoxin and related analogues: Part IX. Synthesis of ethylenedioxy and indian analogues of picropodophyllone and their antimitotic activity", Indian Journal of Heterocyclic Chemistry, vol. 5, No. 3, Jan.-Mar. 1996, pp. 185-188.

Deoxypodophyllotoxin

Podophyllotoxin

Acetylpodophyllotoxin

Epipodophyllotoxin

USE OF CYCLOLIGNANS AND NEW CYCLOLIGNANS

The present invention refers to new compounds as well as to the use of new and known compounds inhibiting the insulin-like growth factor-1 receptor, the IGF-1R, for treatment of IGF-1R dependent diseases, especially cancer.

BACKGROUND OF THE INVENTION

The insulin-like growth factor-1 receptor (IGF-1R) plays an important role in proliferation, protection against apoptosis and transformation of malignant cells. The IGF-1R is also important for maintaining the malignant phenotype of tumour cells, and is involved in tumour cells developing resistance to the action of anti-cancer drugs. In contrast, the IGF-1R seems not to be an absolute requirement for normal cell growth.

The IGF-1R consists of two identical extracellular alpha-subunits that are responsible for ligand binding, and two identical beta-subunits with a transmembrane domain and an intracellular tyrosine kinase domain. The ligand-receptor interaction results in phosphorylation of tyrosine residues in the tyrosine kinase domain, which spans from amino acid 973 to 1229 of the β-subunit. The major sites for phosphorylation are the clustered tyrosines at position 1131, 1135 and 1136 (LeRoith, D., et al., Endocr Rev 1995 April; 16(2), 143-63). After autophosphorylation, the receptor kinase phosphorylates intracellular proteins, like insulin receptor substrate-1 and Shc, which activate the phosphatidyl inositol-3 kinase and the mitogen-activated protein kinase signalling pathways, respectively.

Based on the pivotal role of IGF-1R in malignant cells, it becomes more and more evident that IGF-1R is a target for cancer therapy (Baserga, R., et al., Endocrine vol. 7, no. 1, 99-102, August 1997). One strategy to block IGF-1R activity is to induce selective inhibition of the IGF-1R tyrosine kinase. However, today there are no selective inhibitors of IGF-1R available.

Drugs containing the cyclolignan podophyllotoxin has been used since centuries, and its anti-cancer properties have attracted particular interest. Undesired side effects of podophyllotoxin have, however, prevented its use as an anti-cancer drug. The mechanism for the cytotoxicity of podophyllotoxin has been attributed to its binding to beta-tubulin, leading to inhibition of microtubule assembly and mitotic arrest. The effect of podophyllotoxin on microtubules required μM concentrations in cell free systems. The trans configuration in the lactone ring of podophyllotoxin has been shown to be required for binding to beta-tubulin. In agreement with this, its stereoisomer picropodophyllin, which has a cis configuration in the lactone ring, has a 50-fold lower affinity for microtubuli and a more than 35-fold higher LD50 in rats. Because of the low affinity for microtubuli of picropodophyllotoxin this compound has attracted little interest. During the last decades the major interest on podophyllotoxin derivatives has concerned etoposide, which is a ethylidene glucoside derivative of 4'-demethyl-epipodophyllotoxin. Etoposide, which has no effect on microtubules, is a DNA topoisomerase II inhibitor, and is currently being used as such in cancer therapy. A 4'-hydroxy instead of a 4'-methoxy group of such cyclolignans is an absolute requirement for them to inhibit topoisomerase II.

PRIOR ART

A number of synthetic tyrosine kinase inhibitors, called tyrphostins, have been studied by Párrizas, M., et al., Endocrinology 1997, Vol. 138, No. 4, 1427-1433. The IGF-1R is a member of the tyrosine kinase receptor family, which also includes the receptors of insulin, epidermal growth factor (EGF), nerve growth factor (NGF), and platelet-derived growth factor (PDGF). All of the tyrphostins active on IGF-1R cross-react with the insulin receptor, since they are highly homologous, although two of the tyrphostins showed a moderate preference for IGF-1R. It was therefore suggested that it could be possible to design and synthesize small molecules capable of discriminating between these two receptors.

Substrate competitive inhibitors of IGF-1 receptor kinase are discussed by Blum, G., et al. in Biochemistry 2000, 39, 15705-15712. A number of lead compounds for inhibitors of the isolated IGF-1R kinase are reported. The search for these compounds was aided by the knowledge of the three-dimensional structure of the insulin receptor kinase domain, which is 84% homologous to the IGF-1R kinase domain. The most potent inhibitor found was tyrphostin AG 538, with an IC50 of 400 nM. However, said inhibitor also blocked the insulin receptor kinase.

Kanter-Lewensohn, L., et al., Molecular and Cellular Endocrinology 165 (2000), 131-137, investigated whether the cytotoxic effect of tamoxifen (TAM) on melanoma cells could depend on interference with the expression or function of the insulin-like growth factor-1 receptor. It was found that, although TAM did not have a strong effect on IGF-1 binding and the expression of IGF-1R at the cell surface, at 15 microM TAM efficiently blocked tyrosine phosphorylation of the IGF-1R beta-subunit.

A connection between the IGF-1R and podophyllotoxin derivatives has never previously been made. The Chemistry of Podophyllum by J. L. Hartwell et al., Fortschritte der Chemie organischer Naturstoffe 15, 1958, 83-166, gives an overview of podophyllotoxin and different derivatives thereof, commercially derived from two species of plants, *Podophyllum peltatum* and *Podophyllum emodi*. As said, the observed cytotoxic effect of podophyllotoxin has been ascribed to its binding to microtubuli resulting in a mitotic block. The same effects on cells have been described for deoxypodophyllotoxin and this was suggested to be the reason why these two compounds and their corresponding 4'-demethyl analogues could be used for treatment of psoriasis (WO 86/04062). However, whereas the LD50 of podophyllotoxin in rats is relatively low (14 mg/kg), LD50 of the deoxy derivative is strangely >15-fold higher. Other podophyllotoxin derivatives, for which LD50 in rats was high, such as acetylpodophyllotoxin (185 mg/kg) and epipodophyllotoxin (>200 mg/kg) have been considered to essentially lack biological activity (Seidlova-Masinova V., et al. J Nat Cancer Inst, 18, 359-371, 1957).

Structure-activity evaluation of a number of morpholino derivatives of benzyl-benzodioxole having a structural similarity to podophyllotoxin were performed by Patra, J., et al., Biochemical Pharmacology, Vol. 35, No. 22, 4013-4018, 1986. The ability of the compounds to inhibit tubulin polymerisation was tested, but the morpholino compound most similar to podophyllotoxin was the least active in the series.

Benzyl and cinnamylderivatives of 2,4-di-tert-butylphenol and of 1,3-benzodioxoles are known as insect chemosterilants from Jurd, L., et al., J. Agric. Food Chem. Vol. 27, No. 5, 1007-1016, 1979.

OBJECTS OF THE INVENTION

The object of the invention is to find new compounds and new methods for treatment of IGF-1R dependent diseases, especially cancer, by means of an inhibition of the insulin-like growth factor-1 receptor.

DESCRIPTION OF THE INVENTION

Figure 1:
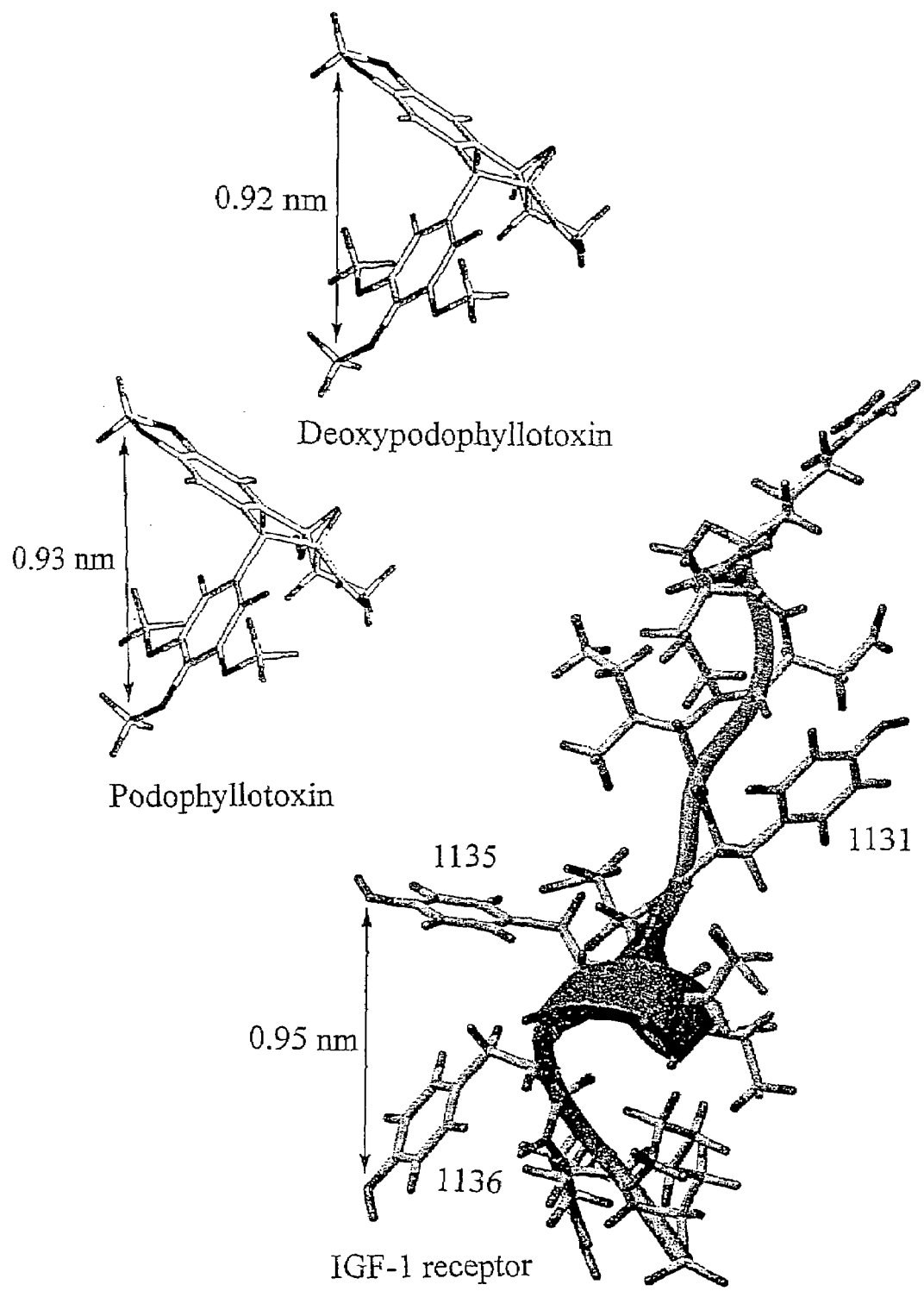
FIG. 1 shows a computer model of the 12 amino acid peptide comprising the tyrosines 1131, 1135 an 1136 of the IGF-1 receptor.
Figure 2A:
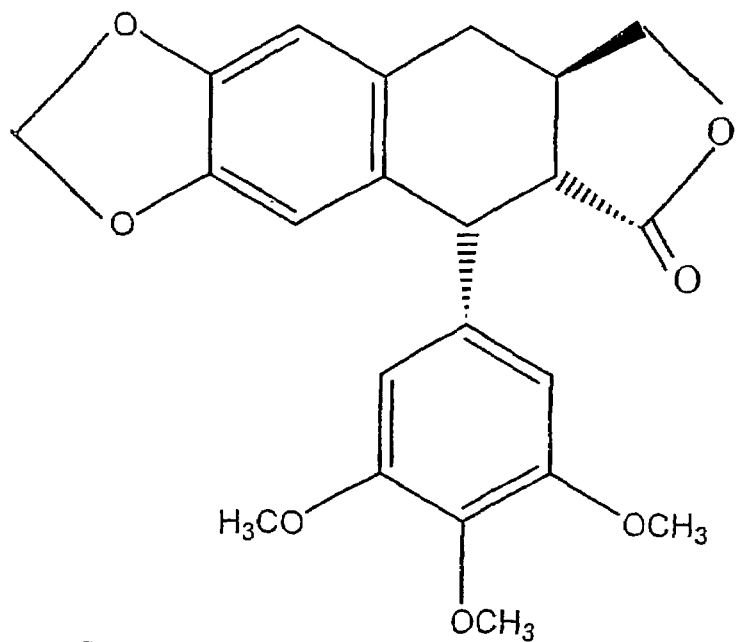
FIG. 2A shows the structural formulas of the compounds podophyllotoxin, deoxypodophyllotoxin.
Figure 2A:
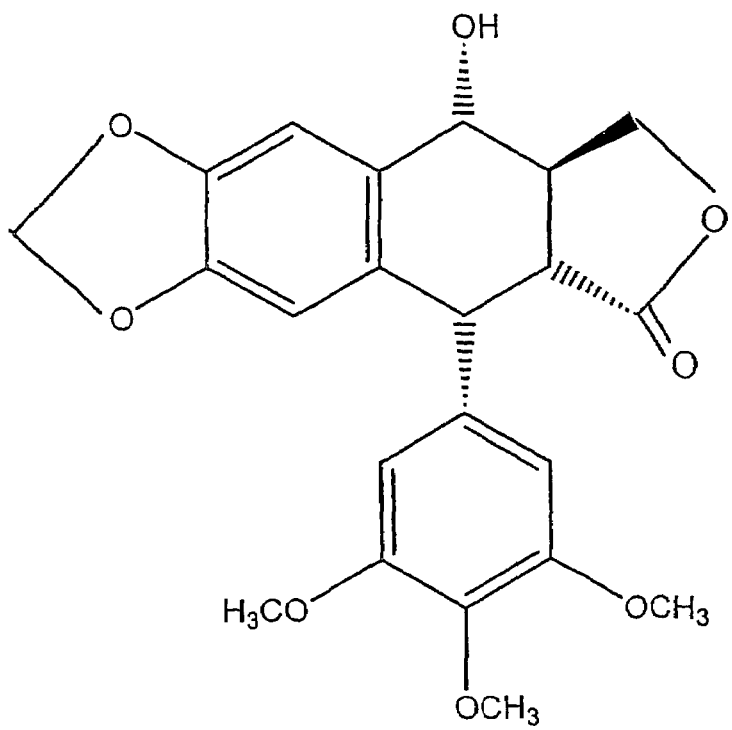
Figure 2B:
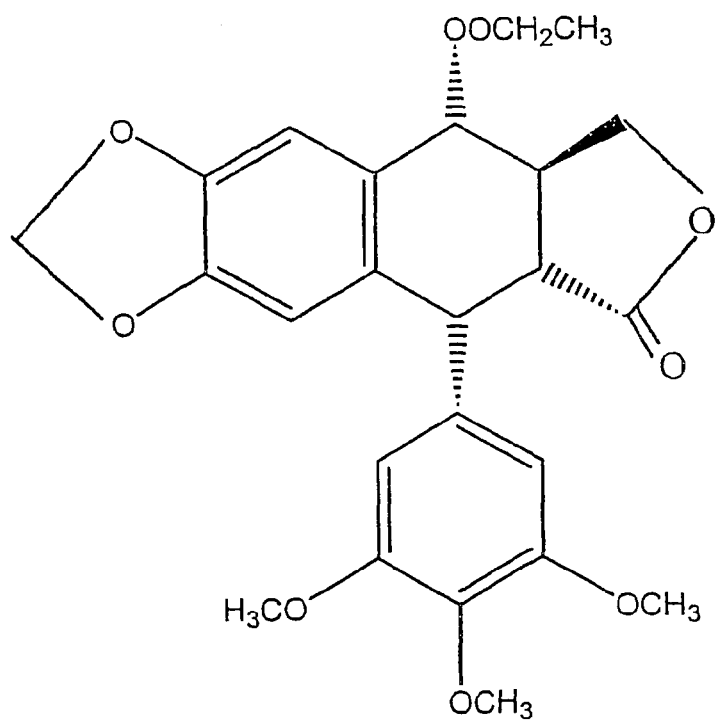
FIG. 2B shows the structural formulas of epipodophyllotoxin and acetylpodophyllotoxin.
Figure 2B:
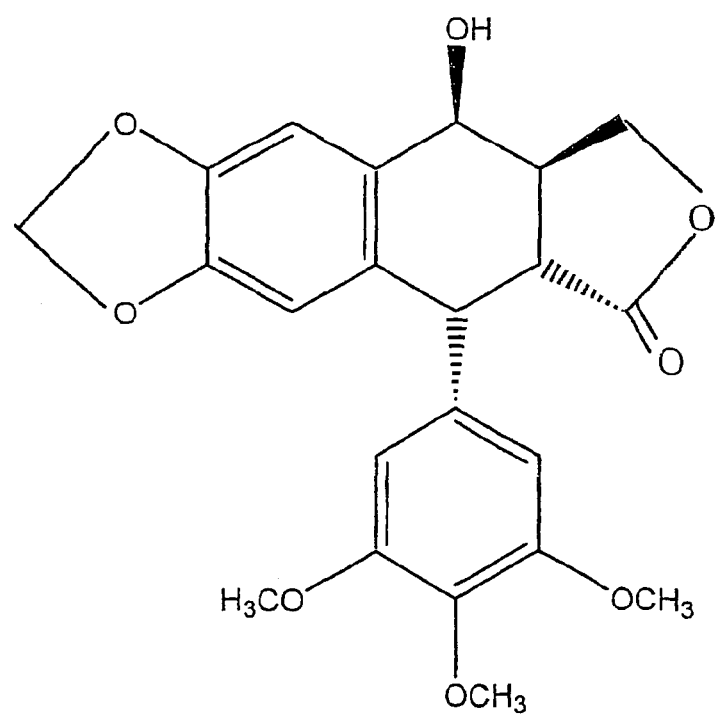

The three-dimensional structure of short peptides having the amino acid sequence of the IGF-1R tyrosine domain, including the tyrosine residues at position 1131, 1135 an 1136, were analysed using a computer programme in order to find compounds having the ability to mimick the tyrosine residues and interfere with their phosphorylation. It was then discovered when using a 12-amino acid peptide that two of the three key tyrosines, that is 1135 and 1136, which have to be autophosphorylated in IGF-1R for activation, could be situated as close as 0.95 nm (9.5 Å) from each other, and that the apparent angle between these groups was about 60°. The configuration of said sequence is shown in FIG. 1. Such a short distance has not been observed for the corresponding tyrosines in the insulin receptor. FIG. 1 also depicts the space structures of podophyllotoxin and deoxypodophyllotoxin.

Molecular modelling showed that an inhibitory molecule could consist of two benzene rings separated by only one carbon atom. When a two-carbon bridge was tried, the distance between the substituents of the benzene rings was too long, about 1.3 nm (13 Å).

The substituents of the inhibitors corresponding to the hydroxy groups in the tyrosines were selected to be methoxy or methylenedioxy groups, since they are chemically relatively stable, i.e. they are not oxidized or phosphorylated. The distance between these substituents should be about 0.95±0.10 nm (9.5±1.0 Å).

It was then surprisingly found that the two angled benzene rings of some cyclolignans, including podophyllotoxin, could mimick almost exactly the two tyrosines 1135 and 1136, indicating that podophyllotoxin and derivatives could interfere with the autophosphorylation of these tyrosine residues.

In order to penetrate the receptor, an inhibitory molecule has to be small. When for instance podophyllotoxin was conjugated with a glucoside derivative, podophyllotoxin-4,6-O-benzylidene-β-D-glucopyranoside, the effect on IGF-1R completely disappeared. Furthermore, following reduction of the lactone ring to a diol structure, the size of the molecule increased due to the reduced substituents sticking out from the molecule, resulting in a dramatically reduced activity of the compounds. Increasing the size by forming methylenedioxy derivatives or acetonides of podophyllotoxindiol also resulted in compounds with little or no activity.

The inhibitor molecule also has to be relatively nonpolar, so that it can freely penetrate cell membranes and the IGF-1 receptor, but sufficiently polar to be reasonably soluble in water. The polarity of the molecule is determined by the number and nature of the oxygen functions. The polarity seems to be optimal when the water solubility is between that of deoxypodophyllotoxin, i.e. about 0.01 mM, and that of podophyllotoxin, about 0.1-0.2 mM. No charged or highly polar groups should be present on the molecule.

The invention refers to the use of a compound comprising the formula

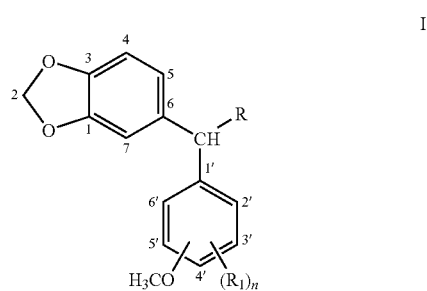

wherein the distance between the carbon atom of the methylene group and the carbon atom of the methoxy group is 0.85-1.05 nm;

R is OH, OCH$_3$, OC$_2$H$_5$ or a C$_{1-5}$ linear or branched hydrocarbon chain, optionally having 1-3 oxygen functions, and optionally forming a bond with the carbon (number 5) in the top benzene ring.

R$_1$, which can be the same or different, is OH or OCH$_3$, and n is 0-2;

as an inhibitor of tyrosine phosphorylation of the insulin-like growth factor-1 receptor.

Oxygen functions in this context refer to hydroxy, oxo, carboxy, methoxy, methylenedioxy, lactone, ether and/or ester groups.

One group of compounds which can be used in accordance with the invention has the formula Ib

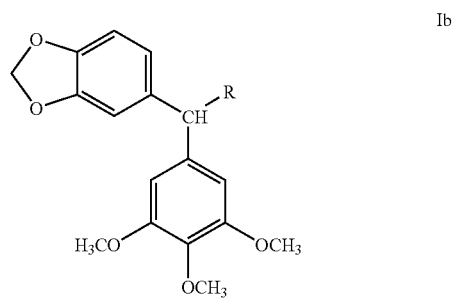

wherein R is OH, OCH$_3$, OC$_2$H$_5$, CH$_3$, C$_2$H$_5$, or C$_2$H$_4$OH; and R$_1$ and n are as defined above. The substituent R of the compounds of this group can be in the R or S position in relation to the bottom benzene ring.

Compounds of the formula I can be prepared by the following representative synthesises:

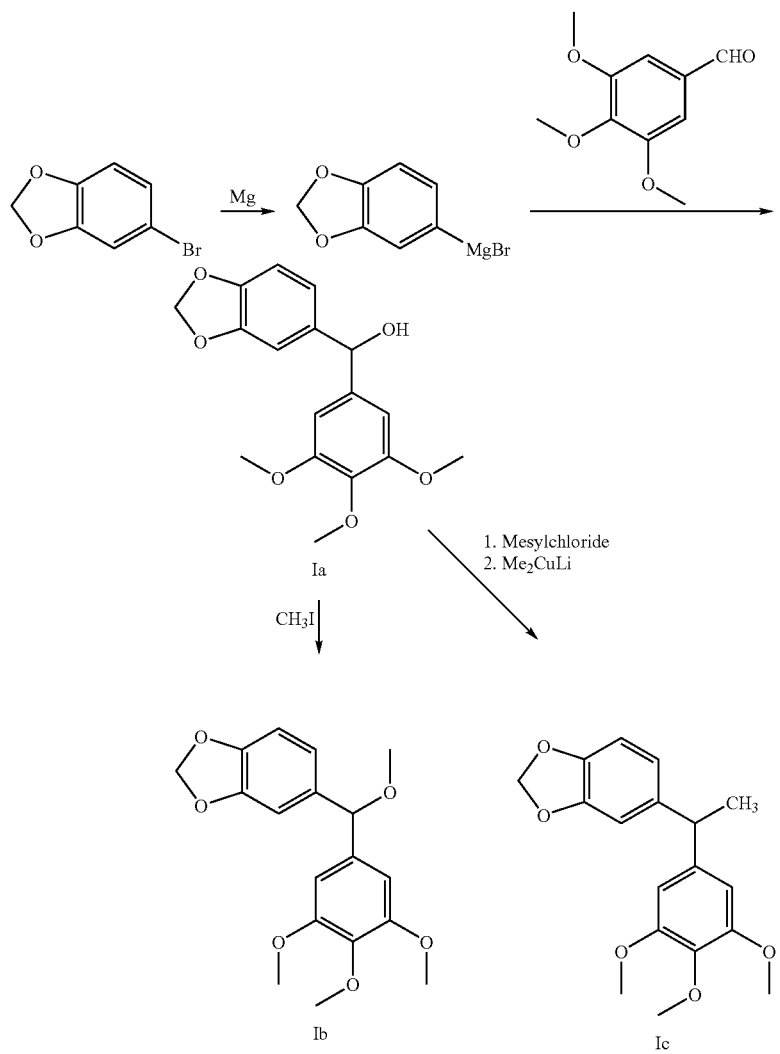

As examples of compounds which can be prepared in this way can be mentioned:
6-(3,4,5-trimethoxy-alpha-hydroxy-benzyl)-1,3-benzodioxole (Ia)
6-(3,4,5-trimethoxy-alpha-methoxy-benzyl)-1,3-benzodioxole (Ib)
6-(3,4,5-trimethoxy-alpha-methyl-benzyl)-1,3-benzodioxole (Ic)

Another group of compounds which can be used in accordance with the invention has the formula II

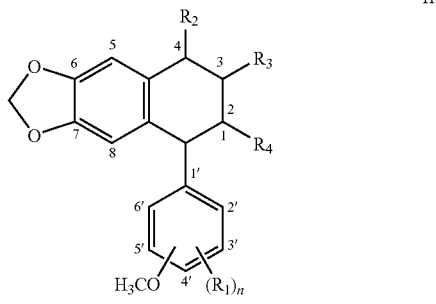

wherein $R_2$, $R_3$ and $R_4$, which can be the same or different, are H, OH, O, $OCH_3$, $OC_2H_5$ or $R_2$ and $R_3$ together is a methylenedioxy group, or $R_3$ and $R_4$ together is an acetonide, carbonate or methylendioxy group; and $R_1$ and n are as defined above. The substituents $R_2$, $R_3$ and $R_4$ can, when not expressing an oxo group, be in either alpha- or beta-position. The bottom benzene ring should preferably be in the alpha-position.

Compounds of the formula II can be prepared by the following representative synthesises:

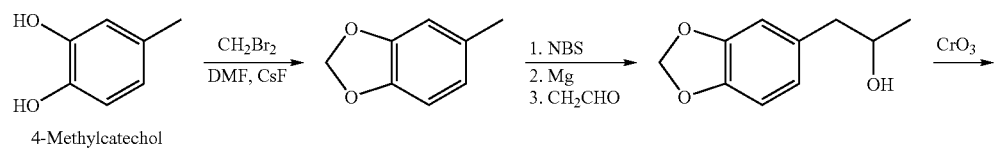
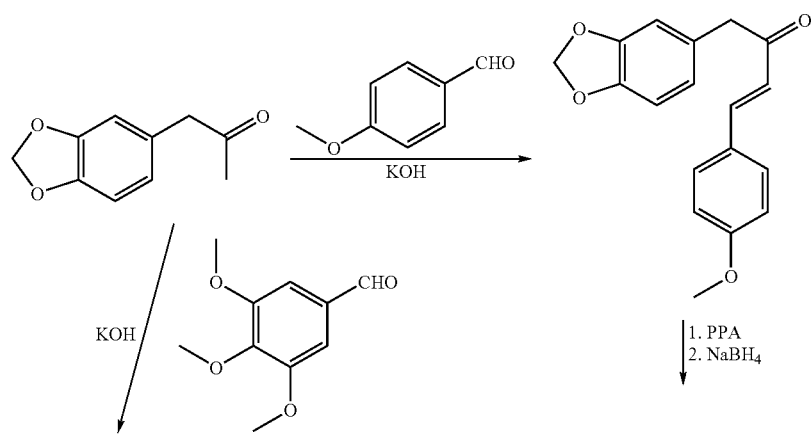
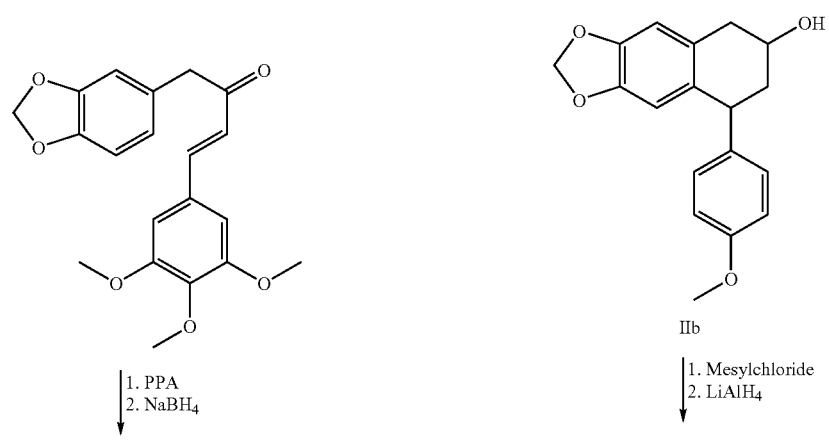
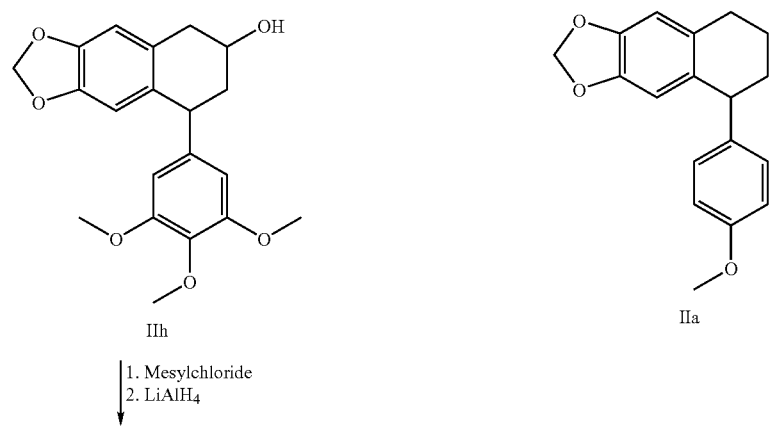

-continued

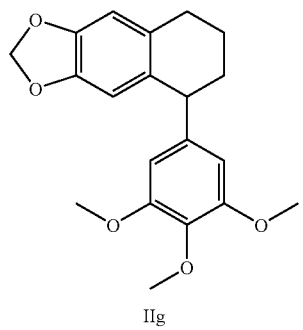

IIg

In said schedules NBS is N-bromosuccinimide, PPA is polyphosphoric acid, TTN is thalliumnitrate trihydrate, p-TSA is p-toluene sulfonic acid, DMF is N,N-dimethylformamide, and LDA is lithium dialkylamide.

As examples of compounds which can be prepared in this way can be mentioned:

1-(4-methoxy-phenyl)-6,7-methylenedioxy-1,2,3,4,-tetrahydronaphtalene (II a)

3-hydroxy-(4 methoxy-phenyl)-6,7-methylenedioxy-1,2,3,4-tetrahydronaphtalene (II b)

1-(3,4,5-trimethoxy-phenyl)-6,7-methylenedioxy-1,2,3,4,-tetrahydronaphtalene (II g)

3-hydroxy-1-(3,4,5-trimethoxy-phenyl)-6,7-methylenedioxy-1,2,3,4-tetrahydronaphtalene (II h).

Compounds of the formula II can also be prepared by the following synthesis:

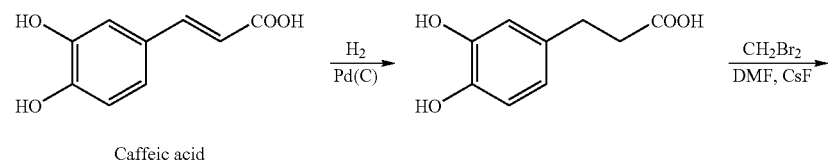

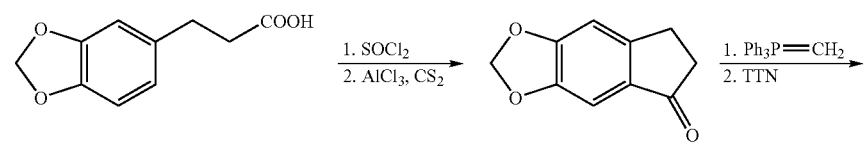

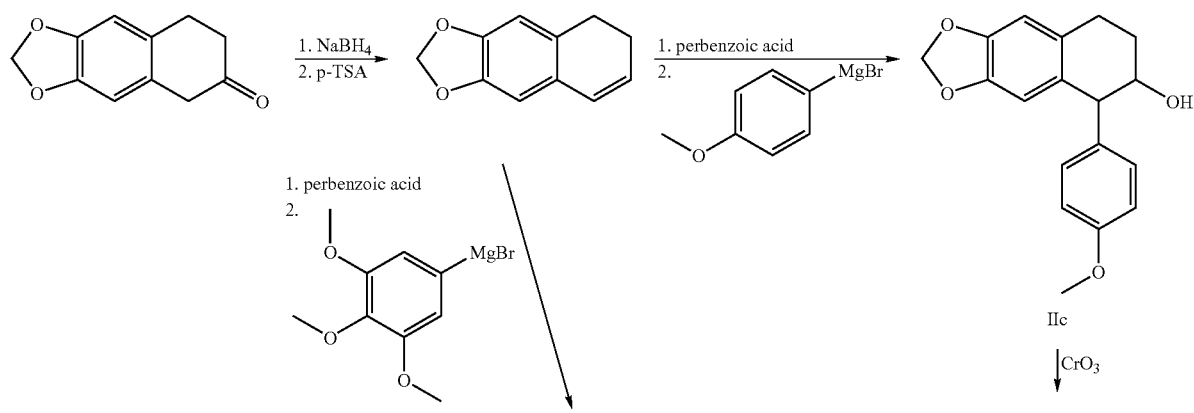

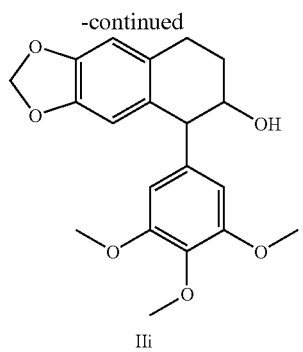

IIi

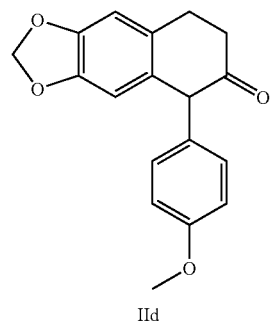

IId

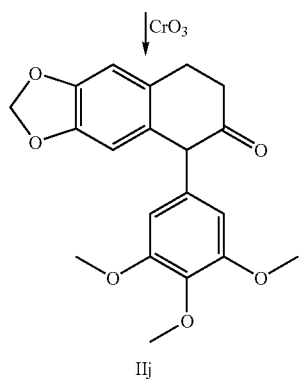

IIj

As examples of compounds which can be prepared in this way can be mentioned:

2-hydroxy-1-(4-methoxy-phenyl)-6,7-methylenedioxy-1,2,3,4-tetrahydronaphtalene (II c)

1-(4-methoxy-phenyl)-2-oxo-6,7-methylenedioxy-1,2,3,4-tetrahydronaphtalene (II d)

2-hydroxy-1-(3,4,5-trimethoxy-phenyl)-6,7-methylenedioxy-1,2,3,4-tetrahydronaphtalene (II i)

1-(3,4,5-trimethoxy-phenyl)-2-oxo-6,7-methylenedioxy-1,2,3,4-tetrahydronaphtalene (II j).

Compounds of the formula II can also be prepared as follows:

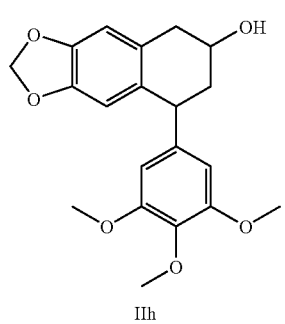

IIh

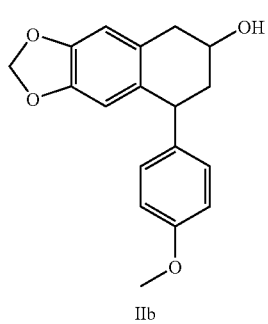

IIb

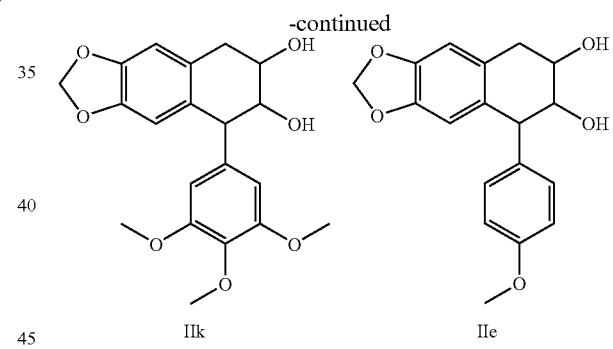

IIk      IIe

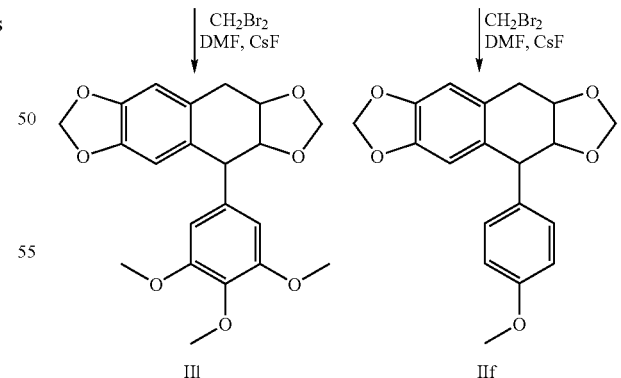

III      IIf

As examples of compounds which can be prepared in this way can be mentioned:

2,3-dihydroxy-1-(4-methoxy-phenyl)-6,7-methylenedioxy-1,2,3,4-tetrahydronaphtalene (II e)

1-(4-methoxy-phenyl)-2,3-methylenedioxy-6,7-methyl-enedioxy-1,2,3,4-tetrahydronaphtalene (II f)

2,3-dihydroxy-1-(3,4,5-trimethoxy-phenyl)-6,7-methyl-enedioxy-1,2,3,4-tetrahydronaphtalene (II k)

1-(3,4,5-trimethoxy-phenyl)-2,3-methylenedioxy-6,7-methylenedioxy-1,2,3,4-tetrahydronaphtalene (II l)

Details of the reaction conditions in the above synthesises are described in Advanced Organic Chemistry, Jerry March (ed.), 4$^{th}$ edition, Wiley-Interscience Publication, New York, 1992.

Still another group of compounds which can be used in accordance with the invention are compounds of the formula III

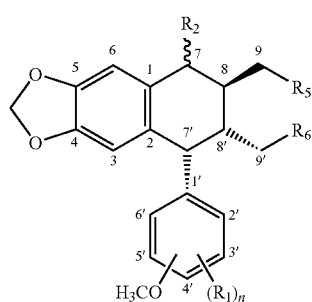

wherein $R_2$, $R_5$, $R_6$, which can be the same or different, are H, OH, OOCH$_3$, OOCH$_2$CH$_3$, OCH$_3$, or OC$_2$H$_5$, or $R_5$ and $R_6$ together is an ether or a lactone; and $R_1$ and n are as defined above. The substituent $R_2$, when being a free hydroxy group cannot be in the alpha-position, as in podophyllotoxin. Other $R_2$ substituents, except an oxo group, can be in either alpha- or beta-position. Notably, the bottom benzene ring is in the alpha-position and there is a beta-bond between the carbons numbered 8 and 9 and an alpha-bond between the carbons numbered 8' and 9', thus they form a trans configuration, as in for example deoxypodophyllotoxin and podophyllotoxin.

The invention especially refers to the use of any of the relatively non-toxic cyclolignans, such as epipodophyllotoxin, deoxypodophyllotoxin and acetylpodophyllotoxin, as an inhibitor of tyrosine autophosphorylation of the insulin growth factor-1 receptor, whereas the use of more cytotoxic and tissue irritating compounds, such as podophyllotoxin and 4'-demethyl-podophyllotoxin, should be avoided.

Some compounds of the formula III are naturally occurring in plants, such as deoxypodophyllotoxin and podophyllotoxin. For the preparation of said substances in pure form, dried and finely ground rhizomes of e.g. *Podophyllum emodi* or *Podophyllum peltatum* are extracted with organic solvents. The extract is then filtered and concentrated on silica gel. The fractions containing the substances are collected and the latter are further purified by chromatography on acid alumina and silica gel etc., and finally recrystallized. Podophyllotoxin may be used as the starting material for the syntheses of its less toxic derivatives.

Epipodophyllotoxin is readily prepared from podophyllotoxin. Five mg of the latter are dissolved in 2.5 mL of acetone. To the solution is added 0,5 mL of concentrated HCl, and the mixture is boiled for 2 hours. The solution is then neutralized with aqueous NaHCO3 (about 0.5 g in 5 mL) and following evaporation of the acetone, the product epipodophyllotoxin is extracted with ethyl acetate.

Acetylpodophyllotoxine (the acetate derivative of podophyllotoxin) can be prepared from podophyllotoxin by incubating 0.1 mg of the latter with 1 mL of acetic anhydride and 1 mL of pyridine at 50° C. for 16 hours. The reagents are then partly evaporated, 10 mL of water and 10 mL of ethyl acetate are added and the product is then extracted from the aqueous phase.

Acetonides and methylenedioxy derivatives can be prepared starting from diols obtained by reducing the lactone ring of natural lignans according to standard procedures.

As additional examples of compounds of the formula III can be mentioned: podophyllotoxone, and 4'-demethyl-deoxypodophyllotoxin.

The invention also refers to the new compounds of the formula I

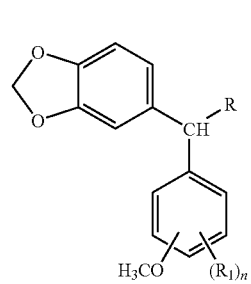

wherein R is OH, OCH$_3$, OC$_2$H$_5$, CH$_3$, C$_2$H$_5$, or C$_2$H$_4$OH; and $R_1$ and n are as defined above, with the proviso that when $R_1$ is OCH$_3$ and n is 2, R is not OH, that when R is a CH$_3$ or C$_2$H$_5$, $R_1$ is OH and n is 1 or 2, that when R is C$_2$H$_5$, $R_1$ is not OH.

The molecule of the invention should be relatively rigid, in order to keep the distance between the two substituents within the given range, that is 0.95±0.10 nm (9.5±1.0 Å). Forming a ring structure of the hydrocarbon chain will prevent rotation or motion, of the benzene ring, and so does lactone formation.

The invention also refers to the new compounds of the formula II

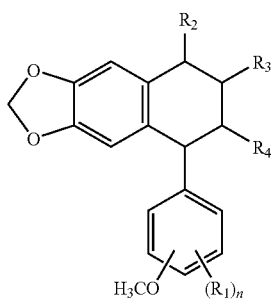

wherein $R_2$, $R_3$ and $R_4$, which can be the same or different, are H, OH, O, OCH$_3$, or $R_2$ and $R_3$ together is a methylenedioxy group, or $R_3$ and $R_4$ together is an acetonide, carbonate or methylendioxy group; and $R_1$ and n are as defined above.

To design an inhibitor of the IGF-1R tyrosine kinase for therapeutic purposes it is of critical importance that the inhibitor does not cross-react with the insulin receptor kinase, which is highly homologous to the IGF-1R. Co-inhibition of the insulin receptor will lead to a diabetogenic response in-vivo. This response comprises a very serious side effect, which cannot be overcome by insulin treatment since the receptor kinase is being blocked. We have demonstrated that podophyllotoxin and derivatives, which are much more potent IGF-1R inhibitors than the tyrophostin-based compounds, do not interfere with the insulin receptor tyrosine kinase at all. Neither do they interfere with tyrosine phosphorylation of the receptors of epidermal growth factor, platelet-derived growth factor or fibroblast growth factor.

Podophyllotoxin has for long been implicated in cancer therapy, but in the way it was administered to patients it produced unacceptable side effects. The anti-cancer effect, as well as the side effects, was attributed to inhibition of microtubule assembly and mitotic block. It has now been demonstrated that podophyllotoxin and some of its less toxic analogues are very potent and specific inhibitors of tyrosine phosphorylation of the insulin-like growth factor-1 receptor, which plays a pivotal role as a survival factor in cancer cells. Compared to the anti-microtubule effect of podophyllotoxin, a 100-fold lower concentrations were sufficient to inactivate the IGF-1R. Of utmost importance is that podophyllotoxin and analogues do not inhibit the insulin receptor, which is highly homologous to IGF-1R. Moreover, they do not inhibit other major growth factor receptor kinases either.

Relatively nontoxic compounds of the formula I can be used for treatment of IGF-1R dependent diseases, such as cancer, arteriosclerosis, including prevention of restenosis of the coronary arteries after vascular surgery, psoriasis and acromegaly.

A pharmaceutical composition comprising a compound of the formula I in combination with a physiologically acceptable carrier and optional additives can be administered to a patient by any suitable route, such as parenterally, preferably by intravenous infusion, or topically, for instance by a patch.

The invention refers to the new compounds of the formula I or II for use as a medicament, and especially for the preparation of a medicament for treatment of cancer.

The results of the biological experiments suggest that submicromolar concentrations of podophyllotoxin, or of less toxic analogues such as deoxypodophyllotoxin or epipodophyllotoxin, can be sufficient to cause tumour cell death. However, it is believed that it is important to keep a constant plasma concentration of the inhibitors over lengthy periods, to allow them to continuously saturate all IGF-1Rs, and in this way eventually kill as many malignant cells as possible. Therefore, continous infusion of podophyllotoxin derivatives, in connection with monitoring the plasma concentration, may be the strategy of treatment instead of repetetive (e.g. daily) injections, which may lead to repeated reactivations of IGF-1R between the treatments.

The invention consequently also refers to a method of treatment of a cancer in a mammal, comprising the steps of administrating a pharmaceutical composition, containing a compound having the formula I in combination with a physiologically acceptable carrier, by constant infusion to a patient suffering from a tumour, controlling the plasma level of the compound, and adjusting the rate of infusion to keep the plasma level between 0.05 and 5.0 µM (depending on the general toxicity of the copound), for a period of time being sufficient for the tumour to be retarded or to disappear.

In case of tumours not completely dependent on IGP-1R, the compounds of the invention can be useful to sensitise the tumour cells to the effects of other anti-cancer drugs.

EXPERIMENTAL

Materials
  Chemicals
  Cell culture reagents, that is media, fetal calf serum and antibiotics, were purchased from Gibco, Sweden. All other chemicals unless stated otherwise were from Sigma (St. Louis. Mo., USA). A mouse monoclonal antibody against phosphotyrosine (PY99) and a polyclonal antibody against α-subunit of IGF-1R (N20) were obtained from Santa Cruz Biotechnology Inc (Santa Cruz, Calif., USA). A monoclonal antibody against the α-subunit of IGF-1R (IR-3) was purchased from Oncogene Science (N.Y., USA). Deoxypodophyllotoxin and podophyllotoxin (99.97% purity), and acetylpodophyllotoxin, podophyllotoxone and 4'-demethylpodophyllotoxin (>95% purity) were obtained as gifts from Analytecon SA, Switzerland.

Cell Cultures
  The human malignant melanoma cell lines SK-MEL-2, SK-MEL-5 and SK-MEL-28, the prostatic carcinoma cell line PC-3, and the breast cancer cell line MCF-7 were from the American Tissue Culture Collection, USA. The malignant melanoma cell lines BE, and FM55 were obtained from Professor R Kiessling, CCK, Karolinska Hospital, Stockholm, Sweden. The R- and P6 cell lines were gifts from Professor R. Baserga, Thomas Jefferson University, Philadelphia, Pa., USA. All cell lines were cultured in Minimal Essential Medium containing 10% faetal bovine serum, glutamine, 1% benzylpenicillin and streptomycin. The cells were grown in monolayers in tissue culture flasks maintained at 95% air/5% $CO_2$ atmosphere at 37° C. in a humidified incubator. For the experiments cells were cultured in either 35-mm or 60-mm plastic dishes or 96-well plastic plates. The experiments were initiated under subconfluent growth conditions.

The human chronic myeloid leukemia K562/S and K562/Vcr30 lines and the acute myeloid leukemia cell lines HL60/0 and HL60/Nov were obtained from ATCC. The K562/S and HL60/0 are wild type (non-resistant) cells, whereas K562/Vcr30 and HL60/Nov are cytostatic-resistant sublines. All leukemia cell lines were cultured in RPMI 1640 medium supplemented with 10% fetal bovine serum and with 2 mM glutamine, 1% benzyl-penicillin and streptomycin. The cells were grown in tissue culture flasks maintained at 95% air/5% $CO_2$ atmosphere at 37° C. in a humidified incubator. For the experiments 25,000 cells were cultured in 60-mm plastic dishes or 96-well plastic plates. The experiments on leukemia cells were performed in collaboration with Associate professor Sigurd Vitols, Department of Pharmacology, Karolinska Hospital (Stockholm, Sweden).

Methods
  Assay of Cell Growth and Survival
  Cell proliferation kit II (Roche Inc.) is based on calorimetric change of the yellow tetrazolium salt XTT in orange formazan dye by the respiratory chain of viable cells (Roehm, N W, et al., J Immunol Methods 142:257-265, 1991). Cells seeded at a concentration of 5000/well in 100 µl medium in a 96-well plate were treated with different drugs in the given concentration. After 24 or 48 h the cells were incubated, according to the manufacturer's protocol, with XTT labelling mixture. After 4 h the formazan dye is quantified using a scanning multiwell spectrophotometer with a 495-nm filter. The absorbance is directly correlated with number of viable cells. The standard absorbance curve was drawn by means of untreated cells seeded at a concentration of from 1000 to 10 000 cells/well with an increasing rate of 1000 cells/well. All standards and experiments were performed in triplicates.

Immunoprecipitation and Determination of Protein Content
  The isolated cells were lyzed in 10 ml ice-cold PBSTDS containing protease inhibitors (Carlberg, M., et al., J Biol Chem 271:17453-17462, 1996). 50 µl protein A or G agarose was added in 1 ml sample and incubated for 15 min at 4° C. on an orbital shaker. After centrifugation for 10 min at 10,000 r/min at 4° C. the supernatant was saved. The protein content was determined by a dye-binding assay with a reagent purchased from Bio-Rad. Bovine serum albumin was used as a standard. 15 μl Protein G Plus agarose and 5 μl anti-IGF-1R were added. After a 3 h incubation at 4° C. on an orbital shaker the precipitate was collected by pulse centrifugation in a micro centrifuge at 14,000×g for 10 s. The supernatant was discarded and the pellet was washed 3 times with PBSTDS.

Sodium Dodecyl Sulphate Polyacrylamide Gel Electrophoresis (SDS-PAGE)

Protein samples were solved in a 2×-sample buffer containing Laemmli buffer and 0.5% methanol and boiled for 5 min at 96° C. Samples were separated by SDS-PAGE with a 4% stacking gel and 7.5% separation gel. Molecular weight markers (Bio Rad, Sweden) were run simultaneously in all experiments.

Western Blotting

Following SDS-PAGE the proteins were transferred overnight to nitro-cellulose membranes (Hybond, Amersham, UK) and then blocked for 1 h at room temperature in a solution of 4% skimmed milk powder and 0.02% Tween 20 in PBS, pH 7.5. Incubations with the primary antibodies were performed for 1 h at room temperature, followed by 3 washes with PBS with Tween and incubation with the second antibody for 1 h room temperature. After another 3 washes the membranes were incubated with Streptavidin-labelled horseradish peroxidase for 30 min and then detected using Amersham ECL system (Amersham, UK) The films were scanned by Fluor-S (BioRad).

Assay of IGF-1R Autophosphorylation in Vitro

IGF-1R tyrosine autophosphorylation was analysed by a sandwich ELISA assay. Briefly, 96-well plates (Immunolon, Nunc) were coated overnight at 4° C. with 1 μg/well of the monoclonal antibody Ab-5 (LabVision) to the IGF-1R beta subunit. The plates were blocked with 1% BSA in PBS Tween for 1 h, then 80 g/well of total protein lysate from the P6 cell line was added. As a negative control was used total protein lysate from R-cell line. The investigated compounds were added in tyrosine kinase buffer without ATP at room temperature for 30 min, prior to kinase activation with ATP. Kinase assay was performed using the Sigma kit. After spectrophotometry the IC50 values of inhibitors were determined using the Regression function of Statistica program.

Experiment 1

Effect of Podophyllotoxin and Other Biologically Active Phenolic Compounds on Phosphorylation of IGF-1R in Cultured Melanoma Cells Melanoma cells (line FM55) were seeded in 6-cm dishes, at a concentration of 10,000 cells/cm$^2$ in Minimal Essential Medium supplemented with 10% fetal calf serum (FCS). When the cells reached a concentration of 65,000 cells/cm$^2$, they were treated with genistein, tamoxifen, quercetin and podophyllotoxin to a final concentration of 0, 1, 15 or 60 μM in the culture medium for 1 h. Treatment with 0 μM represents untreated controls. The cells were then isolated and subjected to immuno-precipitation of the IGF-1R. The immunoprecipitates, containing purified IGF-1R, were fractionated by gel electrophoresis. Phosphorylation of IGF-1R was detected by an anti-phosphotyrosine antibody using Western blotting. The obtained signals represent phosphorylated IGF-1R and the intensity of signals represents amounts of phosphorylated IGF-1R. Details of the methods used are described above. The intensities are quantified by a scanner, which measures the optical density (OD) of the signals. For the control cells the OD is set at 100%. The blank (OD 0%) represents the background. The results given in Table 1 below are mean values of 3 experiments.

TABLE 1

| Level of IGF-1R phosphorylation in intact cells | | | |
|---|---|---|---|
| Compound | 1 μM | 15 μM | 60 μM |
| Genistein | 100 | 96 | 35 |
| Tamoxifen | 95 | 20 | 10 |
| Quercetin | 100 | 105 | 96 |
| Podophyllotoxin | 8 | 4 | 2 |

The results show that podophyllotoxin almost completely blocks IGF-1R phosphorylation at all three concentrations., whereas genistein only has a partial inhibitory effect at 60 μM and quercetin has no effect at all.

Experiment 2

Effect of Podophyllotoxin Derivatives on Autophosphorylation of IGF-1R in Cultured Melanoma Cells FM 55 melanoma cells were cultured in the same way as described in Experiment 1. When reaching a density of 65,000 cells/cm$^2$ in the dishes, they were treated for 1 h with 0.05 μM podophyllotoxin, deoxypodophyllotoxin, acetylpodophyllotoxin, epipodophyllotoxin, 4'-demethylpodophyllotoxin and podophyllotoxone. The cells were then harvested for assay and quantification of IGF-1R autophosphorylation as described above. The values shown in Table 2 represent means of 3 experiments.

TABLE 2

| Inhibitory effect on IGF-1R autophosphoryl-ation in intact cells in relation to podophyllotoxin | |
|---|---|
| Compound | Relative potency |
| Podophyllotoxin | 1 |
| Deoxypodophyllotoxin | 0.8 |
| Acetylpodophyllotoxin | 1.3 |
| Epipodophyllotoxin | 0.5 |
| 4'-demethylpodophyllotoxin | 0.5 |
| Podophyllotoxone | 0.3 |

The results show that acetylpodophyllotoxin, podophyllotoxin, and deoxypodophyllotoxin are potent inhibitors of IGF-1R phosphorylation.

Experiment 3

Dose-response Effects of Podophyllotoxin and Deoxypodophyllotoxin on Viability of Solid Tumour Cells 5 different types of cell lines were seeded in 96-well plates (medium volume in a well was 100 μl), at a concentration of 10,000 cells/cm$^2$ in Minimal Essential Medium supplemented with fetal calf serum. When the cells had reached a concentration of 65,000 cells/cm$^2$, they were treated with different doses of podophyllotoxin and deoxypodophyllotoxin for 48 h. Cell viability was then assayed (see above). IC50 values for each inhibitor and cell line, calculated as the concentration, resulting in a 50% decrease in cell survival, are shown below. The results are based on 4 different experiments.

TABLE 3

IC50 (µM) for cell viability

| Cell line | Origin | Podophyllotoxin | Deoxypodophyllotoxin |
|---|---|---|---|
| SK-MEL-28 | melanoma | 0.05 | 0.04 |
| BE | melanoma | 0.05 | nd |
| FM55 | melanoma | 0.04 | 0.04 |
| MCF-7 | Breast cancer | 0.07 | 0.03 |
| PC-3 | prostate cancer | 0.06 | nd | nd, not determined

This shows that podophyllotoxin and deoxypodophyllotoxin are both very potent inhibitors of tumor cell viability.

Experiment 4

Dose-response Effects of Different Podophyllotoxin Analogues

FM55 melanoma cells were cultured in the same way as described in Experiment 3 and were treated with different doses of podophyllotoxin analogues as described in Experiment 3. The results (IC50 values) are given in the following Table 4.

TABLE 4

IC50 (µM) for viability of FM55 cells

| Compound | IC50 |
|---|---|
| Podophyllotoxin | 0.05 |
| Deoxypodophyllotoxin | 0.04 |
| Acetylpodophyllotoxin | 0.03 |
| 4'-demethylpodophyllotoxin | 0.04 |

The result shows that the tested analogues were all potent.

Experiment 5

Dose-response Effects of Podophyllotoxin Analogues on Viability of Leukemia Cell The leukemia cell lines K562/S, K562/Vcr30, HL60/0 and HL60/Nov were proven to express the IGF-1R. This was assayed by Western blotting analysis, as described in Methods and Experiment 1 and 2. The 4 leukemia cell lines were seeded in 96-well plates (medium volume in a well was 100 µl), in RPMI40 medium supplemented with fetal calf serum. After 24 h podophyllotoxin, deoxypodophyllotoxin and other derivatives were added at different concentrations for 72 h. Cell viability was then assayed (see above). IC50 values for each inhibitor and cell lines are shown below (Table 5). The results are based on 3 different experiments.

TABLE 5

IC50 (nM) for viability of leukemia cell lines

| | K562/S | K562/Vcr30 | HL60 | HL60/Nov |
|---|---|---|---|---|
| Podophyllotoxin | 4 | 7 | 3 | 2 |
| Deoxypodophyllotoxin | 3 | 4 | 3 | 2 |
| Acetylpodophyllotoxin | 80 | 140 | 48 | 46 |
| Epipodophyllotoxin | 195 | 450 | 127 | 90 |
| Podophyllotoxone | >500 | >500 | >500 | >500 |
| 4'-Demethylpodophyllotoxin | 22 | 50 | 20 | 18 |

The results demonstrate that deoxypodophyllotoxin has an unexpected and exceptionally strong cytotoxic effect on human leukemia cells. Such an effect can not be explained solely by its action on IGF-1R. The effects of acetylpodophyllotoxin and epipodophyllotoxin are as expected for an IGF-1R inhibitor.

CONCLUSION

It has been demonstrated that certain cyclolignans such as podophyllotoxin and some analogues deoxypodophyllotoxin are highly specific and potent inhibitors of the IGF-1R tyrosine kinase, as assayed in intact cells. When administered to intact cells the EC50 value was as low as 0.02-0.06 µm.

Podophyllotoxin-induced inactivation of the insulin-like growth factor-1 receptor caused extensive cell death in malignant cells, whereas cells devoid of insulin-like growth factor-1 receptors were resistant. The non-toxic derivative picropodophyllin was equipotent to podophyllotoxin in inhibiting the insulin-like growth factor-1 receptor activity and inducing cell death. This new mechanism of podophyllotoxin and derivatives may be useful in therapy of cancer and other IGF-1R dependent diseases.

The invention claimed is:

1. A compound of formula (I):

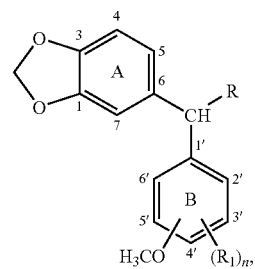

wherein R forms a bond to the carbon at position 5 on ring A and is selected from the group consisting of:
—CH(CH$_2$OH)CH(OH)—,
—CH(COOCH$_3$)CH(OH)—,
—CH(COOCH$_3$)CH$_2$—,
—CH(CH$_2$OH)CH$_2$—,
—CH$_2$CH$_2$—,
—C(CH$_2$)CH(OH)—, and
—CH(CH$_3$)CH(OH)—; and
R$_1$ is OH or OCH$_3$, and
n is 0, 1 or 2.

2. The compound of claim 1, wherein R$_1$ is only OH.

3. The compound of claim 1, wherein R$_1$ is only OCH$_3$.

4. The compound of claim 1, wherein n is 2 and R$_1$ is OH and OCH$_3$.

5. The compound of claim 1, wherein n is 2 and R$_1$ is OCH$_3$.

6. The compound of claim 1, wherein n is 0.

7. A composition comprising the compound of claim 1 and a pharmaceutically acceptable carrier.

8. A compound of formula (I):

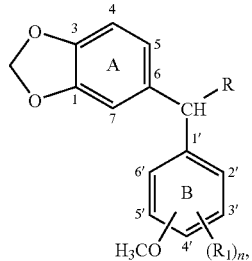

wherein

R is a $C_2$-$C_4$ linear or branched hydrocarbon chain optionally having 1-3 oxygen functions which may form a bond with carbon atom number 5 in ring A; and $R_1$ is OH or $OCH_3$, and n is 0, 1 or 2.

9. The compound of claim 8, wherein R is a $C_2$-$C_4$ linear or branched hydrocarbon chain having 1-3 oxygen functions.

10. The compound of claim 8, wherein R forms a bond with carbon atom number 5 in ring A.

* * * * *

UNITED STATES PATENT AND TRADEMARK OFFICE
CERTIFICATE OF CORRECTION

| | | |
|---|---|---|
| PATENT NO. | : 7,709,526 B2 | Page 1 of 1 |
| APPLICATION NO. | : 11/346294 | |
| DATED | : May 4, 2010 | |
| INVENTOR(S) | : Olle Larsson et al. | |

It is certified that error appears in the above-identified patent and that said Letters Patent is hereby corrected as shown below:

On the title page, Item (73), the Assignee information is incorrect. Item (73) should read:

-- (73) Assignee: Axelar AB, Stockholm, (SE) --

Signed and Sealed this
Twenty-second Day of February, 2011

David J. Kappos
*Director of the United States Patent and Trademark Office*